United States Patent [19]

Webster, Jr.

[11] Patent Number: 4,535,757
[45] Date of Patent: Aug. 20, 1985

[54] AUTOINFLATABLE CATHETER

[76] Inventor: Wilton W. Webster, Jr., 1388 Crest Dr., Altadena, Calif. 91001

[21] Appl. No.: 371,727
[22] PCT Filed: Mar. 12, 1982
[86] PCT No.: PCT/US82/00319
§ 371 Date: Apr. 26, 1982
§ 102(e) Date: Apr. 26, 1982
[87] PCT Pub. No.: WO83/03204
PCT Pub. Date: Sep. 29, 1983

[51] Int. Cl.³ .................. A61M 25/00; A61M 29/00
[52] U.S. Cl. ................................ 128/1 D; 604/102; 604/104
[58] Field of Search ............. 128/1 D; 604/101–104, 604/96, 132–133, 53

[56] References Cited

U.S. PATENT DOCUMENTS

| Re. 4,726 | 1/1872 | Mattson | 604/104 |
|---|---|---|---|
| 68,096 | 8/1867 | Mattson | 604/104 |
| 1,879,305 | 9/1932 | Kennedy | 128/344 |
| 3,435,826 | 4/1969 | Fogarty | 128/348.1 |
| 3,467,101 | 9/1969 | Fogarty et al. | 128/348.1 |
| 3,557,794 | 1/1971 | Van Patten | 128/345 |
| 3,568,659 | 3/1971 | Karnegis | 128/1 D |
| 3,585,983 | 6/1971 | Kantrowitz et al. | 128/1 D |
| 3,592,184 | 7/1971 | Watkins | 128/1 D |
| 3,889,686 | 6/1975 | Duturbure | 604/102 |
| 4,019,515 | 4/1977 | Kornblum et al. | 604/101 |
| 4,261,339 | 4/1981 | Hanson et al. | 128/1 D |
| 4,276,874 | 7/1981 | Wolvek et al. | 604/96 X |
| 4,292,974 | 10/1981 | Fogarty et al. | 128/344 |
| 4,304,239 | 12/1981 | Perlin | 128/642 |
| 4,327,709 | 5/1982 | Hanson et al. | 128/1 D |
| 4,346,698 | 8/1982 | Hanson et al. | 604/103 X |
| 4,402,307 | 9/1983 | Hanson et al. | 128/1 D |

FOREIGN PATENT DOCUMENTS

| 2707951 | 9/1977 | Fed. Rep. of Germany | 128/1 D |
|---|---|---|---|
| 0933375 | 8/1963 | United Kingdom | 604/96 |

Primary Examiner—Lee S. Cohen
Assistant Examiner—Angela D. Sykes
Attorney, Agent, or Firm—Christie, Parker & Hale

[57] ABSTRACT

An autoinflatable catheter is disclosed which comprises an elongated first catheter tube section forming a main catheter body, a short second catheter tube section forming a catheter tip, a balloon support extending between the posterior end of the catheter tip and the anterior end of the main catheter body and an inflatable balloon surrounding the balloon support. The balloon support comprises a rigid cage having a continuous hollow interior and openings for the flow of liquid through the cage to inflate the balloon. The openings are sufficiently large to not significantly restrict the flow of liquid through the openings and to prevent pooling of liquid in the chamber between the cage and the balloon.

15 Claims, 2 Drawing Figures

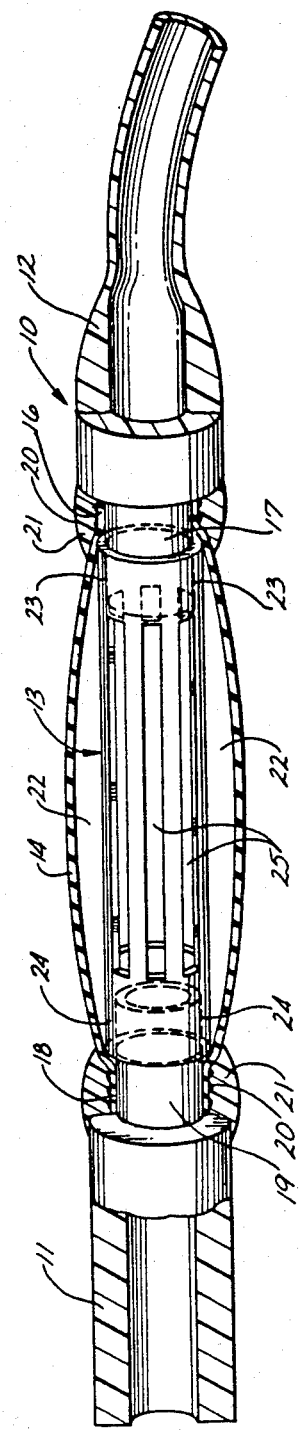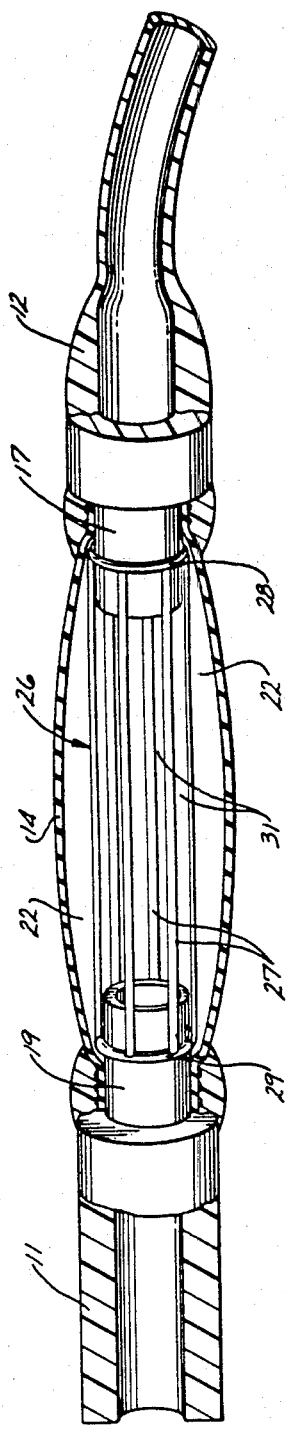

AUTOINFLATABLE CATHETER

FIELD OF THE INVENTION

This invention pertains to catheters for use in the blood vessels of humans, as well as in animals generally. More particularly, it pertains to a blood pumping retroperfusion catheter featuring an improved balloon support structure enabling blood to be used effectively as a balloon inflation fluid without damage to the blood for such purpose.

BACKGROUND OF THE INVENTION

A new medical technique for heart attack patients involves the pulsatile retroperfusion of oxygenated blood into the myocardium from the coronary sinus. The procedure comprises advancing an autoinflatable catheter into the coronary sinus. During diastole, oxygenated blood is pumped through the catheter into the coronary sinus. The blood flowing through the catheter is under sufficient pressure to inflate the balloon which is also positioned in the sinus. Inflation of the balloon blocks a portion of the sinus which results in the unidirectional retroperfusion of oxygenated blood from the catheter through coronary veins into the myocardium. During systole, no blood is pumped through the catheter which, as a result, deflates the balloon and allows coronary venous blood to drain past the collasped balloon. Oxygenated blood is continuously pumped to the myocardium by this method until such time as the coronary arteries can be repaired.

For this procedure to operate efficiently, the balloon of the catheter must be inflatable and deflatable in a very short period of time. Typical inflation times are on the order of 50 milliseconds. This requires the free flow of blood into and out of the balloon chamber.

Some conventional autoinflatable catheters utilize holes in the catheter tube to form passages into the balloon chamber formed between the balloon and the catheter tube through which the blood flows for inflating and deflating the balloon. The number and size of the holes are sufficiently small to not significantly weaken the catheter tube. However, the small size of the holes may cause significant damage to the blood. This is because a portion of the blood flowing through the holes and contacting the catheter wall may be damaged by the contact. The amount of damage to the blood is related to the amount of blood contacting the catheter wall as it flows into the balloon chamber, which in turn is dependent on the size of the holes.

In addition, the small size of the holes tends to restrict the free flow of blood into and out of the balloon chamber resulting in undesirably slow inflation and deflation of the balloon. To compensate, increased pressure may be used, resulting in faster inflation of the balloon, but may further damage the blood as it passes through the holes. Furthermore, a small number of holes create regions in the balloon chamber where blood tends to stagnate and possibly clot.

There are other catheters which utilize an axial rod between two catheter tube sections as a balloon support. One end of the balloon is attached to each catheter tube section. This catheter design enables free flow of a liquid within the interior of the balloon but results in obstructions in each catheter tube section at the positions where the axial rod is attached to the catheter tube sections. These obstructions restrict the amount of the liquid flowing through the catheter tube to inflate the balloon. As such, catheters having an axial rod as a balloon support are not suitable for applications such as the retroperfusion of blood to the myocardium.

SUMMARY OF THE INVENTION

In accordance with the invention, there is provided a balloon support suitable for allowing rapid inflation and deflation of the balloon of an autoinflatable catheter.

The balloon support is attachable between two sections of a catheter tube and comprises a rigid cage having open anterior and posterior ends and a continuous hollow interior. The anterior end of the cage is attachable to the posterior end of one catheter tube section and the posterior end of the cage is attachable to the anterior end of the other catheter tube section. The cage has open ends and thereby forms an unobstructed pathway between the two catheter tube sections.

The cage further comprises openings for forming passages between the interior of the cage and a balloon chamber formed between the cage and a balloon positioned surrounding the cage. The openings are sufficiently large not to significantly restrict the flow of a liquid, such as blood, through the openings. The openings are also sufficiently large to substantially prevent pooling of liquid in the balloon chamber.

In a preferred embodiment, the cage comprises a plurality of spaced generally-parallel rods. The rods are connected at each end to rings which are attachable about the ends of the catheter tube sections. The spaces between adjacent rods form openings which are sufficiently large not to significantly restrict the flow of a liquid through the openings and to substantially prevent pooling of a liquid in the balloon chamber. It is particularly preferred that the cage be constructed from stainless steel wire.

In another preferred embodiment, the cage comprises a rigid slotted tube. The anterior end of the cage is attachable about the posterior end of one catheter tube section and the posterior end of the cylinder is attachable about the anterior end of the other tube section. The cage has open anterior and posterior ends and slots in the cage wall forming openings which are sufficiently large not to significantly restrict the flow of a liquid through the openings and to substantially prevent pooling of liquid in the balloon chamber.

A preferred autoinflatable catheter comprising a balloon support constructed according to the principles of the invention comprises an elongated first catheter tube section that forms a main catheter body. The main catheter body is connected by the balloon support to a short second catheter tube section that forms a catheter tip. A balloon surrounds the balloon support forming a balloon chamber between the balloon and the balloon support and is sealed at one end around the catheter tip and at the other end around the main catheter body. Free flow of a liquid, such as blood, into and out of the balloon chamber through the ballon support enables rapid inflation and deflation of the balloon. Furthermore, the openings of the balloon support substantially eliminate pooling of the liquid in the balloon chamber. In the case of liquids such as blood which may be damaged, the openings are sufficiently large to minimize the damage to such liquids due to contact with the cage wall.

BRIEF DESCRIPTION OF THE DRAWINGS

These and other features and advantages of the present invention will be better understood by reference to the following detailed description when considered in conjunction with the accompanying drawings wherein:

FIG. 1 is a fragmentary, partially cutaway, sectional view of an autoinflatable catheter showing a preferred embodiment of a balloon support; and FIG. 2 is a fragmentary, partially cutaway, sectional view of an autoinflatable catheter showing another preferred embodiment of a balloon support.

DETAILED DESCRIPTION

The present invention is particularly suited to a process for the pulsatile retroperfusion of oxygenated blood into the myocardium of a heart attack patient from the venous side.

In such a process, a puncture is made into a large artery, e.g., the brachial artery in the patient's arm, using a hypodermic needle. A tube connects the hypodermic needle to a pulsatile pump which is driven by air pressure. The anterior end of an autoinflatable catheter constructed according to principles of this invention is inserted into a vein, e.g., the exterior jugular vein, and advanced into the coronary sinus part of the heart so that the catheter balloon is positioned in the coronary sinus. The posterior end of the catheter is attached to the pulsatile pump.

Oxygenated blood flows from the punctured artery through the hypodermic needle and tube to the pulsatile pump and is then delivered pulsatilely during diastole through the catheter to the coronary sinus. A portion of the blood flowing through the catheter inflates the balloon, thereby blocking a portion of the coronary sinus. The remainder of the oxygenated blood flows through the catheter into the coronary sinus where it retroperfuses into the myocardium, thereby providing at least a portion of the oxygen supply that has been cut off from the coronary arteries. During systole, blood is not pumped through the catheter and the balloon deflates, thus allowing deoxygenated venous blood to drain through the coronary sinus.

A preferred embodiment of an autoinflatable catheter, used in the retroperfusion of blood to the myocardium, constructed according to principles of the present invention, is shown in FIG. 1. The catheter 10 comprises an elongated flexible catheter tube section forming a main catheter body 11 and a short flexible catheter tube section forming a hollow catheter tip 12 which is connected to the main catheter body by a balloon support 13. The main catheter body and the catheter tip have generally circular cross-sections and substantially the same outer diameter ranging from about 0.080 inch to about 0.120 inch.

The inner diameter of the catheter tip is smaller at the anterior end than at the posterior end. The difference in the inner diameter between the anterior and posterior ends of the catheter tip is sufficient to create a pressure drop in a liquid flowing through the catheter. The magnitude of the pressure drop is sufficient to cause the balloon to inflate when a liquid is pumped through the catheter at a select pressure. In this application, blood is pumped through the catheter at about 2 psi (about 100 mm Hg). The catheter tip creates a pressure drop of about 1 psi (about 50 mm Hg) which is sufficient to inflate the balloon. The anterior end of catheter tip 12 is open for the flow of blood into the coronary sinus.

To minimize the increase in the diameter of the catheter due to the thickness of the balloon support and balloon at the junctures where they are mounted to the main catheter body and the catheter tip, the thickness of the wall of the anterior end 19 of the main catheter body and the posterior end 17 of the catheter tip may be reduced as shown in FIG. 1.

An inflatable and deflatable balloon 14 surrounds the balloon support. The balloon may be a non-elastomeric bag or bladder or an elastomeric balloon. The anterior end 16 of the balloon is sealed about the outer circumference of the posterior end 17 of the catheter tip 12 and the posterior end 18 of the balloon is sealed about the anterior end 19 of the main catheter body 11. The seals prevent leakage of liquid from the catheter. The seals may be made by conventional methods, e.g., tying with nylon thread 20 and then overlaying the juncture with a compatible adhesive 21 or by solvent evaporation techniques. The balloon forms a balloon chamber 22 between the balloon support and the balloon wall.

The balloon support 13 comprises a generally cylindrical tubular cage of about 0.40 inch (about one centimeter) in length but may vary from about 0.2 inch to about 0.6 inch. The cage has open anterior and posterior ends and a hollow interior, thereby forming an unobstructed pathway between the main catheter body and the catheter tip. The inner diameter of the cage ranges from about 0.060 inch to about 0.100 inch, depending on the outer diameters of the anterior end of the main catheter body and the posterior end of the catheter tip.

The cage is constructed of a rigid material which may be metallic or non-metallic. The material is compatible with the liquid, e.g., blood in this application, flowing through the catheter. The material is also sufficiently strong to maintain a rigid shape under the conditions of use. This prevents crimping of the cage with a concomitant restriction of the blood flow through the cage. The presently preferred balloon supports are constructed from stainless steel. However, other compatible metals and rigid plastics are also suitable.

The inner diameter of the cage is about equal to the outer diameter of the posterior end of the catheter tip and the anterior end of the main catheter body. The anterior end 23 of the cage is attached about the posterior end 17 of the catheter tip 12 at a position posterior to the balloon-catheter tip seal using adhesive compatible with the cage, the catheter tip and the patient's blood, e.g., a polyurethane adhesive. The posterior end 24 of the cage is attached in the same manner about the anterior end 19 of the main catheter body 11 and is positioned anterior to the balloon-main catheter body seal. This construction completely encloses the cage within the balloon.

The cage comprises openings or slots 25 in the wall of the cage, forming passages between the interior of the cage 13 and the balloon chamber 22 sufficiently large to not significantly restrict the flow of a liquid through the openings. In this application, the openings are large enough to enable blood to flow into the balloon chamber sufficiently rapidly to inflate the balloon and block the coronary sinus during diastole and to flow out of the balloon chamber sufficiently rapidly to deflate the balloon during systole, thereby allowing drainage of blood through the coronary sinus without significantly damaging the blood. The balloon is inflated in about 50 milliseconds to provide effective retroperfusion of oxygenated blood into the myocardium.

The slots 25 extend lengthwise a distance sufficient to substantially prevent pooling of the blood, i.e., the formation of stagnant regions of blood, in the balloon chamber 21. In the preferred embodiment, as shown in FIG. 1, the cage comprises six slots. Each slot is about 0.280 inch in length and has a circumferential width of about 0.025 inch. This leaves about 0.060 inch on each end of the cage for bonding to the catheter tube sections. Thus, approximately fifty percent of the circumferential area between the main catheter body and the catheter tip defines openings into the balloon chamber.

The slots in the cage wall may be made by electron discharge machining (EDM), followed by electrochemical machining to remove sharp edges. These processes do not alter the stainless steel metallurgy. The metallurgical properties of the cage are therefore controlled by selection of the appropriate grade of stainless steel tubing.

Another preferred embodiment of an autoinflatable catheter applicable to such a procedure is shown in FIG. 2. In this embodiment, a main catheter body 11 and a catheter tip 12 of similar construction as previously described for the embodiment shown in FIG. 1 are connected by a balloon support 26. A balloon 14 is positioned surrounding the support balloon and is attached to the main catheter body and catheter tip also as described in the previous embodiment.

The balloon support 26 comprises a plurality of spaced generally-parallel rods 27 defining a generally cylindrical shape. The rods are attached at their anterior ends to a first generally-circular ring 28 and at their posterior end to a second generally-circular ring 29. The rods and rings may be made of metal or non-metal material. It is presently preferred that the rods and rings are made of stainless steel wire having an outer diameter about 0.010 inch. Attachment of the ends of the rods to the rings is preferably made by welding to form a strong bond. However the welding may alter the metallurgy of the stainless steel in the immediate area of the weld. If the altered metallurgy is incompatible with the liquid, e.g., blood, flowing through the cathether, this method of attachment would be unsuitable.

The rings have an inner diameter substantially the same as the outer diameter of the posterior end of the catheter tip and the anterior end of the main catheter body, generally from about 0.060 inch to about 0.100 inch. The anterior ring 28 is attached about the posterior end 17 of the catheter tip 12 and the posterior ring 29 is attached about the anterior end 19 of the main catheter body 11. Attachment is made by a compatible adhesive. The thickness of the wall of the main catheter body at its anterior end and of the catheter tip at its posterior end may be reduced as shown to minimize the increase in catheter diameter at these positions.

The rods are sufficiently strong to supply the stiffness required by the cage to prevent bending and crimping. The rods are spaced apart sufficiently to form openings 31 between the interior of the support cage 26 and the balloon chamber 21 that do not significantly restrict passage of liquid into and out of the balloon chamber. In addition, the openings extend completely between the main catheter body and the catheter tip, thereby effectively preventing pooling of a liquid in the balloon chamber. The size of the openings is sufficient to minimize damage to liquids such as blood passing through the openings.

For catheters having non-circular cross-sections, the embodiments shown in both FIG. 1 and FIG. 2 may be modified for use in such catheters. The cross-sectional configuration of the cage is formed into a configuration corresponding to the cross-sectional shape of the catheter tube sections.

If the main catheter body has a different cross-sectional configuration than the catheter tip, the rod and ring cage construction as shown in FIG. 2 is preferred because the anterior and posterior rings may be formed into different shapes to correspond to the catheter tube section to which they attach.

In addition to applications such as the retroperfusion of blood to the myocardium, an autoinflatable catheter constructed according to the present invention may be used in other applications such as the delivery of saline plus an intervention to a patient.

The preceding description has been presented with reference to the presently preferred embodiments of the invention shown in the accompanying drawings. Workers skilled in the art and technology to which this invention pertains will appreciate that alterations and changes in the described apparatus can be practiced without meaningfully departing from the principles, spirit and scope of this invention. Accordingly, the foregoing description should not be read as pertaining only to the precise structures described, but rather should be read consistent with and as support for the following claims which are to have their fullest fair scope.

What is claimed is:

1. An autoinflatable catheter comprising:
   a. an elongated first catheter tube section having open anterior and posterior ends forming a main catheter body;
   b. a short second catheter tube section having open anterior and posterior ends forming a catheter tip having a smaller cross-sectional area at its anterior end than at its posterior end;
   c. a balloon support comprising a rigid cage having an open anterior end connected to the posterior end of the catheter tip, an open posterior end connected to the anterior end of the main catheter body and a continuous hollow interior forming an unobstructed pathway between the main catheter body and the catheter tip, said cage having openings through the cage intermediate the cage ends for the flow of a liquid between the interior of the cage and the balloon chamber formed between the cage and a balloon positioned in a surrounding relation to the cage, said openings being sufficiently large not to significantly restrict the flow of a liquid through the openings and to prevent pooling of liquid in the balloon chamber; and
   d. an inflatable and deflatable balloon surrounding the balloon support having an anterior end sealed about the posterior end of the catheter tip and a posterior end sealed about the anterior end of the main catheter body.

2. An autoinflatable catheter as claimed in claim 1 wherein the cage comprises a plurality of spaced substantially-parallel rods connected at their anterior ends to a ring attached about the posterior end of the first catheter tube section and connected at their posterior ends to a ring attached about the anterior end of the second catheter tube section.

3. An autoinflatable catheter as claimed in claim 1 wherein the cage comprises a rigid slotted tube having an anterior end attached about the posterior end of the first catheter tube section and a posterior end attachable about the anterior end of the second catheter tube section.

4. In an autoinflatable catheter comprising a first catheter tube section having open anterior and posterior ends, a second catheter tube section having open anterior and posterior ends, a balloon support having an anterior end connnected to the posterior end of the first catheter tube section, a posterior end connected to the anterior end of the second catheter tube section and a balloon positioned in a surrounding relation to the balloon support having an anterior end sealed about the posterior end of the first catheter tube section and a posterior end sealed about the anterior end of the second catheter tube section wherein the first catheter tube section provides a sufficient pressure drop to inflate the balloon when a liquid is caused to flow through the catheter at a minimum select pressure, the improvement wherein the balloon support comprises a rigid cage having open anterior and posterior ends and a continuous hollow interior forming an unobstructed pathway between the first catheter tube section and the second catheter tube section and openings through the cage intermediate the cage ends forming passages for the flow of a liquid between the interior of the cage and the balloon, said openings being sufficiently large to not significantly restrict the flow of a liquid through the openings and to substantially prevent pooling of liquid between the balloon and the cage.

5. A catheter as claimed in claim 4 wherein the cage comprises a rigid slotted tube having an anterior end attached about the posterior end of the first catheter tube section and a posterior end attached about the anterior end of the second catheter tube section.

6. A catheter as claimed in claim 4 wherein the cage comprises a plurality of spaced substantially-parallel rods connected at their anterior ends to a ring attached about the posterior end of the first catheter tube section and connected at their posterior ends to a ring attached about the anterior end of the second catheter tube section.

7. An autoinflatable catheter for the retroperfusion of blood comprising:
   a. an elongated first catheter tube section having open anterior and posterior ends and a generally circular cross-section forming a main catheter body;
   b. a short second catheter tube section forming a catheter tip having open anterior and posterior ends and a generally circular cross-section wherein the cross-sectional area at the anterior end is smaller than at the posterior end and wherein the diameter at the posterior end is substantially the same as the anterior end of the main catheter body;
   c. a generally cylindrical balloon support comprising a rigid cage having an open anterior end connected to the posterior end of the catheter tip, an open posterior end connected to the anterior end of the main catheter body and a continuous hollow interior forming an unobstructed pathway between the main catheter body and the catheter tip, said cage having openings intermediate its ends from its interior to a balloon chamber formed between the cage and a balloon positioned in a surrounding relation to the cage, said openings being sufficiently large to not significantly restrict the flow of blood through the openings and to prevent pooling of blood in the balloon chamber and to minimize damage to the blood from movement into and out of the balloon chamber; and
   d. an inflatable and deflatable balloon surrounding the balloon support having an anterior end sealed about the outer circumference of the posterior end of the catheter tip and a posterior end sealed about the outer circumference of the anterior end of the main catheter body.

8. A catheter as claimed in claim 7 wherein the cross-sectional area of the catheter tip is sufficiently smaller at its anterior end than at its posterior end to create a pressure drop of about 1 psi when blood is caused to flow through the catheter at a pressure of about 2 psi.

9. A catheter as claimed in claim 7 wherein the cage has an inner diameter of from about 0.060 inch to about 0.100 inch.

10. A catheter as claimed in claim 7 wherein the cage is from about 0.2 inch to about 0.6 inch in length.

11. A catheter as claimed in claim 7 wherein the cage comprises a rigid slotted cylindrical tube having an anterior end attached about the posterior end of the catheter tip and a posterior end attached about the anterior end of the main catheter body.

12. A catheter as claimed in claim 5 wherein the slots in the cylindrical tube comprise about one-half of the circumferential area of the cage between the catheter tube sections.

13. A catheter as claimed in claim 7 wherein the cage comprises a plurality of spaced substantially parallel rods connected at their anterior ends to a ring attached about the posterior end of the catheter tip and connected at their posterior ends to a ring attached about the anterior end of the main catheter body.

14. A catheter as claimed in claim 13 wherein the rods and rings are constructed from stainless steel wire.

15. A catheter as claimed in claim 14 wherein the stainless steel wire has an outer diameter of about 0.010 inch.

* * * * *